United States Patent
Newman

[11] 3,979,274
[45] Sept. 7, 1976

[54] MEMBRANE FOR ENZYME ELECTRODES

[75] Inventor: David P. Newman, Yellow Springs, Ohio

[73] Assignee: The Yellow Springs Instrument Company, Inc., Yellow Springs, Ohio

[22] Filed: Sept. 24, 1975

[21] Appl. No.: 616,326

[52] U.S. Cl. ............... 204/195 B; 204/195 P; 204/296; 195/103.5 R; 195/103.5 C; 428/213; 156/230; 210/490; 210/500 M
[51] Int. Cl.² .......................... G01N 27/46
[58] Field of Search ......... 204/195 R, 195 P, 195 B, 204/1 E, 296; 195/103.5 R, 103.5 C; 210/490, 500 M; 428/213

[56] References Cited
UNITED STATES PATENTS

| | | | |
|---|---|---|---|
| 3,098,813 | 7/1963 | Beebe et al. | 204/195 P |
| 3,539,455 | 11/1970 | Clark | 204/195 P |
| 3,542,662 | 11/1970 | Hicks et al. | 204/195 P |
| 3,575,836 | 4/1971 | Sternberg | 204/195 P |
| 3,707,455 | 12/1972 | Derr et al. | 204/195 P |
| 3,718,563 | 2/1973 | Krull et al. | 204/195 P |
| 3,776,819 | 12/1973 | Williams | 204/195 B |
| 3,838,033 | 9/1974 | Mindt et al. | 204/195 P |
| 3,869,354 | 3/1975 | Montalvo | 204/195 B |

OTHER PUBLICATIONS

Clark et al., "Annals of the New York Academy of Science", vol. 102, pp. 29–45, (1962).

Primary Examiner—T. Tung
Attorney, Agent, or Firm—Biebel, French & Nauman

[57] ABSTRACT

A laminated membrane for use with an enzyme electrode without the need for use of a compensating electrode. The laminated membrane comprises a layer of essentially homogeneous material such as cellulose acetate or silicone rubber which will prevent passage of even low molecular weight interfering materials, an adhesive layer of the enzyme itself (with or without other materials that may be blended with it), and a layer of support film which will also prevent the passage of high molecular weight interfering materials.

9 Claims, 2 Drawing Figures

MEMBRANE FOR ENZYME ELECTRODES

BACKGROUND OF THE INVENTION

This invention relates to an improved membrane for an enzyme electrode, and more particularly to a laminated membrane wherein the enzyme itself (with or without other materials blended with it) is used as the adhesive between the lamina.

Polarographic cell systems have become quite popular in the medical field for measurement of various substances. In addition, enzymes have been used in conjunction with polarographic cells, especially in instances where the unknown substance to be measured is not polarographically active, but a material produced or consumed by an enzymatic reaction with that unknown is detectable. For example, it is known that glucose is not polarographically active but that the following reaction takes place in the presence of the enzyme glucose oxidase:

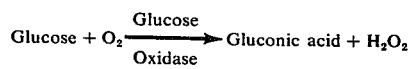

$$\text{Glucose} + O_2 \xrightarrow{\text{Glucose Oxidase}} \text{Gluconic acid} + H_2O_2$$

The existence of this reaction is significant in enabling polarographic measurement of glucose.

Thus, in an article by Clark and Lyons in the *Annals of the New York Academy of Science*, 102, 29–45 (1962), it was suggested that a pH sensitive electrode could be used to detect the gluconic acid produced by the reaction. It was disclosed that the enzyme in such a system could be trapped between Cuprophane membranes. The glucose diffuses through the membrane and is converted by the enzyme to gluconic acid, which then diffuses both toward the pH sensitive glass and back into the donor solution.

Alternatively, it was suggested that by using a hydrophobic membrane, a dialysis membrane, glucose oxidase, and a $pO_2$ electrode, a system could be arranged that is sensitive to glucose by virtue of the fact that oxygen is consumed from the flowing glucose solution in proportion to its glucose content.

Later, Clark obtained a patent on an improvement in such a system. In U.S. Pat. No. 3,539,455, it is stated that the system disclosed therein "differs in simplicity, reliability and in function from the cell disclosed in 'Annals of the New York Academy of Sciences'". Rather than measuring the pH change or the oxygen consumption, the Clark patent discloses using a platinum anode to measure the hydrogen peroxide produced. In the polarographic cell described in that patent, the enzyme is placed on the anode side of a cellophane membrane. The low molecular weight glucose passes through the membrane and reacts with the enzyme, but interfering high molecular weight catalase and peroxidase materials do not. It is disclosed that the enzymes may be held in a thin film directly between the platinum surface and the membrane by placing the enzyme on a porous film which has spaces large enough to hold enzyme molecules. The use of polymeric gels to stabilize the enzyme is also disclosed.

Since the cellophane membrane will not prevent low molecular weight interfering materials such as uric acid or ascorbic acid from reaching the anode, Clark suggests a dual electrode system. The compensating electrode, without an enzyme present, gives a signal for the interfering substances while the enzyme electrode detects both the hydrogen peroxide and the interference. By subtracting the reading of the compensating electrode from that of the glucose electrode, the amount of hydrogen peroxide production, and thus, the glucose level is determined. Still, such a dual sensor system may encounter difficulties in the matching of the two cells.

Under the circumstances, then, it would be desirable to have an enzyme electrode which employs a thin filter membrane to prevent passage of even low molecular weight interfering materials, such as uric acid and ascorbic acid, while permitting hydrogen peroxide to pass therethrough with minimum hindrance. There exist membrane materials, such as silicone rubber and cellulose acetate, which permit passage of hydrogen peroxide but which are effective barriers to interfering substances. Since this type of membrane must be placed between the anode and some component of the sensing system, it follows that in order for measurement equilibrium to be as rapid as possible, the membrane must be as thin as possible while still retaining its selectivity. In the case of a hydrogen peroxide sensing probe, this membrane will need to be less than 2 microns thick. A membrane of this thickness is difficult, if not impossible to use in practice because of its insufficient strength.

Some support is needed. Depositing the material in a thin layer on a porous substructure will be in some respects satisfactory. The porous substructure will provide the necessary strength while at the same time being of little hindrance to hydrogen peroxide passage, and the weak interference rejecting layer can be thin to enhance speed of response. It remains that this laminated membrane be combined with a polarographic electrode and appropriate enzyme in such a fashion that the completed sensor responds satisfactorily to the desired non-polarographic substrate. In a common configuration with a typical membrane, the enzyme is placed between the anode and membrane as disclosed in the Clark patent. With the laminated membrane just described, the enzyme in this configuration would be as effectively shielded as the anode. Therefore the interference rejection must be limited to molecules the same size or larger than the substrate of the enzyme. Membrane materials that would reject smaller interferences would also prevent the substrate from reaching the enzyme.

Alternatively, the enzyme may be placed on the side of this laminated membrane away from the anode. In this case it may be captured by a third outer membrane layer which is permeable to the substrate but impermeable to the enzyme. In this configuration, the substrate is not unnecessarily hindered from reaction with the enzyme, and good interference rejection is possible since the filter layer need pass only the resultant polarographic substance, i.e., hydrogen peroxide. The polarographic substance, however, is now produced two layers away from the sensing anode, being separated from it by the thin interference-rejecting layer and the porous substructure, and speed of response is limited by the reservoir effect of this spacing.

As a further alternative, the enzyme may be placed within the porous substructure and captured by an outer membrane, but this configuration also has the limitations on speed imposed by the multiple layers, and specifically by the thickness of the porous substructure, for now the enzyme is dispersed in this thick layer and is less accessible to its substrate.

As a still further alternative, the enzyme may be placed within and bonded to the porous substructure so that the third outer membrane may be eliminated. Thus, the polarographic substance, hydrogen peroxide, is produced close to the anode and the enzyme is readily accessible to its substrate. This approach, however, requires very sophisticated enzyme immobilization techniques, and presents difficulties in the control of the diffusion of the substrate which determines the range of linearity of the electrode.

Another problem with such a membrane is that if it is too thin it will not have sufficient strength; whereas, if it is too thick, then the all-important speed of measurement is lengthened beyond that tolerable.

That is, for measurement of the unknown in any one sample, time is consumed while the reaction takes place and the potentiometer equilibrates and records the amount of $H_2O_2$ produced. Then, before another sample can be tested the potentiometer must go back down to the null point. As is apparent, when a large number of samples are to be analyzed, any reduction in this time period is quite significant.

Accordingly, the need exists for an enzyme electrode membrane which will prevent passage of both high and low molecular weight interfering chemicals, and does not require an inordinant amount of time for sample measurement.

SUMMARY OF THE INVENTION

In accordance with the present invention there is provided a laminated, two-ply membrane wherein an enzyme adhesive is used to bond the two plys together. The membrane includes (1) a support layer which controls substrate diffusion and serves as a barrier to high molecular weight substances, (2) an enzyme preparation for reacting with the unknown and for bonding the layers together, and (3) an essentially homogeneous layer which serves as a barrier to interfering low molecular weight materials, but permits hydrogen peroxide to pass through. All of this can be achieved in a total membrane thickness preferably less than around 10 microns, although somewhat thicker membranes, up to around 25 microns, are contemplated. As such, the laminated membrane of the present invention is capable of equilibrating speeds as low as 10 seconds when used with a polarographic cell such as that disclosed in Clark U.S. Pat. No. 3,539,455.

When used with an enzyme electrode, the layer nearest the anode is a silicone rubber, methyl methacrylate, cellulose acetate or other material which will prevent passage of interfering chemicals such as ascorbic acid and uric acid. This layer may be less than 2 microns thick and preferably has a thickness of between 0.5 and 1.0 microns. The layer nearest the sample is a diffusion barrier which prevents passage of high molecular weight substances while at the same time providing the tensile strength to hold the shape of the membrane and maintain intimate contact with the electrode. This material is preferably a porous polycarbonate, but may be of other types such as metal mesh. It has a preferred thickness of less than 20 microns, more preferably of between 1 and 10 microns, and most preferred of between 5 and 7 microns.

The adhesive bonding these two layers together is an enzyme preparation, i.e., glucose oxidase, glactose oxidase, uricase, etc., which may be mixed with, for instance, gluteraldehyde. It is placed in a thin uniform layer from an aqueous paste or solution onto an essentially homogeneous film which is supported on a carrier sheet. A self-sustaining support film is then brought into contact with the enzyme preparation on the substrate to form a laminate. The laminate is then dried to adhesively set the enzyme preparation and securely bond the layers together. The membrane may be used in this form after the carrier is removed. Alternatively, for easy application onto a polarographic cell, an appropriately sized O-ring may be glued onto the support layer surface, individual laminated membranes punched out of the sheet, and the carrier layer removed from each.

Accordingly, it is an object of the present invention to provide an improved laminated membrane for use in an enzyme electrode.

Other objects and advantages of the invention will be apparent from the following description, the accompanying drawing and the appended claims.

BRIEF DESCRIPTION OF THE PREFERRED EMBODIMENT

Figure 1:
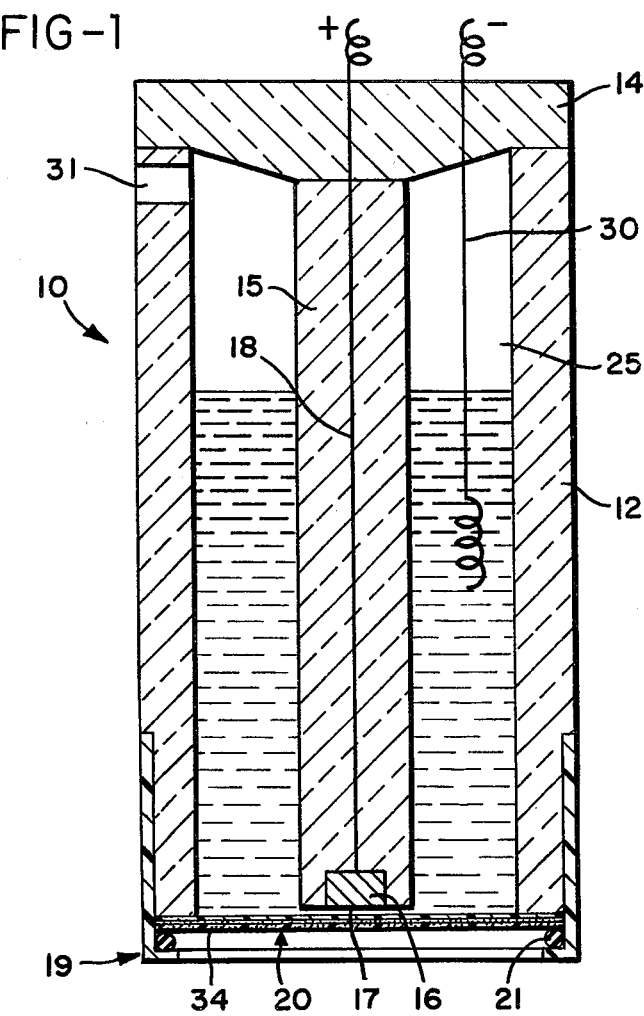
FIG. 1 is a view partly in section and partly in elevation of a polarographic cell having in place the laminated membrane of the present invention.

Referring to FIG. 1, there is shown a cell assembly which includes an electrically insulating support body 12 of plastic or glass which is preferably cylindrical and which is convered by an electrically insulating cap 14. Positioned within the cylindrical body 12 is an electrically insulating member or rod 15 of plastic or glass which supports a platinum electrode 16, the latter including an active or exposed face 17, and a conductor 18 attached to the electrode 16 and which passes through the rod 15 and through the cap 14.

The lower end of the support body 12 is provided with an annular ring or retainer 19, and a laminated membrane 20 in accordance with the present invention is supported over the end of the supporting body nearest the electrode 16 and spaced a capillary distance from the active face 17. The membrane is held in position on the supporting body by an O-ring 21 or the like.

An annular space 25 is provided between the rod 15 and the supporting body 12 and receives a reference electrode 30 which may for example be silver chloride coated silver wire. The space 25 is at least partly and preferably completely filled with a liquid mixture of electrolyte which contacts both electrodes 30 and 16 and which may be introduced into the chamber through an aperture 31 provided beneath the cap 14.

In polarographic measurements two electrodes are commonly used, one of which is polarized and does not allow current to flow until depolarized by a substance being measured. In the cell structure shown in FIG. 1, electrode 30 is the cathode and is polarized and frequently referred to as the reference electrode. The other electrode, electrode 16 as shown in FIG. 1, functions as an anode and is not polarized in the presence of the substances being measured and therefore will not restrict the flow of relatively large current and is frequently referred to as the sensor electrode. The electrodes as shown in FIG. 1 are in electrically insulating relation, and the electrolyte material which occupies the chamber 25 provides an electrical path between the two electrodes. Typical electrolytes include sodium or potassium chloride buffers including carbonate, phosphate, bicarbonate, acetates, or alkali or rare earth salts, or other organic buffers or mixtures thereof. The solvent for such electrolyte may be water, glycols, glycerine, and mixtures thereof.

A more detailed description of the enzyme electrode itself, exclusive of the laminated membrane of the present invention, is found in Clark U.S. Pat. No. 3,539,455, which is hereby incorporated by reference.

Figure 2:
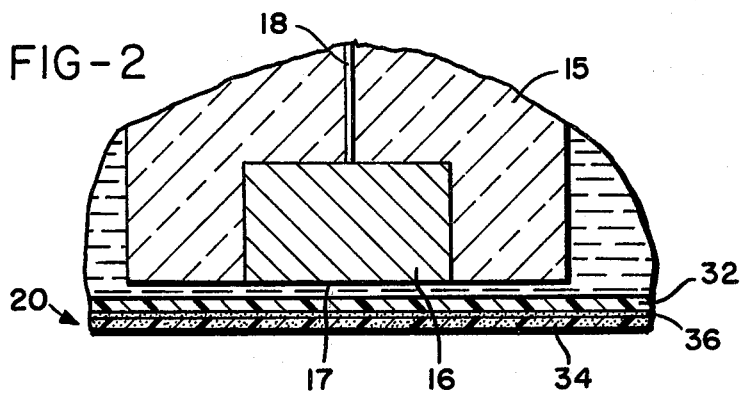
FIG. 2 is an enlarged view of the lower central portion of the polarographic cell of FIG. 1 and showing in more detail the laminated membrane of the present invention.

FIG. 2 shows membrane 20 more fully and will be referred to primarily in the description of that membrane. Layer 32, as shown, is that adjacent the active face 17 of anode 16. That layer is the essentially homogeneous silicone, methyl methacrylate or cellulose acetate material. Layer 34 is the outer layer which will be in contact with the sample to be analyzed. In the preferred embodiment, this is a 0.03 micron pore size perforated polycarbonate film having a thickness of 5 microns, a nitrogen flow rate of 25 ml/min/cm$^2$ at 10 psi, and having $6 \times 10^8$ holes/cm$^2$. Such films are available from Nuclepore Filtration Products of Pleasanton, Calif. When an approximately 5–7 micron thick support film is used, the overall thickness of the laminated membrane is less than 10 microns as is preferred. Typical thicknesses would be 5 microns for layer 34, 1 micron for layer 32, and one micron for layer 36, or a total of 7 microns thickness. Layer 36 is the adhesive enzyme material bonding layers 32 and 34 together.

The laminated membrane 20 is preferably produced by first placing the essentially homogeneous layer on a strippable carrier sheet. In the case of cellulose acetate, this is done by depositing the cellulose acetate in a solvent (cyclohexanone, for example) solution onto water. A film forms which can be picked up by a strippable carrier sheet such as polyethylene. A similar process can be used for silicones and other essentially homogeneous materials such as methyl methacrylate. As mentioned, the preferred thickness for the essentially homogeneous layer is in the range of 0.5 to 1.0 microns.

The enzyme preparation may be simply a mixture of an appropriate enzyme such as glucose oxidase, glactose oxidase, etc. in water. Of course, other materials such as a binder or a cross-linking agent like gluteraldehyde may be included in the enzyme preparation. Likewise, the proportion of enzyme to water in the preparation is immaterial as long as flowable paste or solution is formed which may be coated or pressed easily into a thin uniform layer, and sufficient enzyme is incorporated to provide an adequate reactive amount for measurement.

After placing the aqueous enzyme solution or paste onto the essentially homogeneous layer, a self-sustaining support sheet of diffusion barrier material 34, preferably a porous polycarbonate, is brought into contact with the enzyme preparation on the cellulose acetate layer to form a laminate. The laminate is then dried by allowing it to sit in air at room temperature for a half-hour or more. Additionally, to condition the laminate for transit and storage it may be baked at 45°C for approximately half-an-hour. When the carrier sheet is removed the laminated membranes are ready for installation onto a polarographic cell.

However, if preferred, the laminating procedure may be followed by gluing onto the support layer 34 a rubbery O-ring 21 of an appropriate size for fitting into the retainer 19 on the polarographic cell 10 (see FIG. 1). Laminated membranes 20 ready for use may then be punched out around the O-rings. Of course, the support layer is stripped off the face of the essentially homogeneous layer in this case, too.

As ready for use and in use, the laminated membrane 20 need not be kept moist since the bond between layers 32 and 34 will withstand the differential expansion caused by drying. That is, drying of the laminate will not cause cracking or other destruction of the interference rejecting layer.

Most significantly, because the laminated membrane may be less than 10 microns in thickness, less than 30 seconds (and even in some cases as few as 10 seconds) is taken for a polarographic analysis. During that short period of time the unknown and oxygen diffuse through layer 34, react with the enzyme in layer 36, and then the hydrogen peroxide formed diffuses through layer 32 to contact the active face 17 of the anode 16. The potentiometer then equilibrates in the measurement of the amount of hydrogen peroxide. This quick measurement time is extremely important to laboratories and hospitals where numerous analyses must be made each day.

While the article and method herein described constitute preferred embodiments of the invention, it is to be understood that the invention is not limited to this precise article and method, and that changes may be made therein without departing from the scope of the invention.

What is claimed is:

1. A polarographic cell structure for use in polarographic analysis of an unknown comprising an electrically insulating support means, and electrode means mounted in said support means, said electrode means including means defining an active exposed working face, wherein the improvement comprises:
 a laminated membrane of a total thickness of less than 25 microns positioned between said working face and said unknown, said membrane consisting essentially of a first layer of an essentially homogeneous material selected from the group consisting of silicone rubber, methyl methacrylate, and cellulose acetate and having a thickness of less than 2 microns, a second layer of a support material which permits passage of low molecular weight substances but excludes high molecular weight substances, said support material having a thickness of between 1 and 20 microns, and an enzyme preparation positioned between and adhesively bonding said first and second layers.

2. A polarographic cell structure as set forth in claim 1 wherein the essentially homogeneous material is cellulose acetate having a thickness of 0.5 to 1.0 micron.

3. A polarographic cell structure as set forth in claim 2 wherein said enzyme is selected from the group consisting of glucose oxidase, glactose oxidase, and uricase.

4. A polarographic cell structure as set forth in claim 3 wherein said second layer is a porous polycarbonate film having a thickness of approximately 5–7 microns and the overall thickness of said membrane is less than 10 microns.

5. A laminated membrane having a total thickness of less than 25 microns for use in a polarographic cell consisting essentially of a first layer of essentially homogeneous material selected from the group consisting of silicone rubber, methyl methacrylate and cellulose acetate and having a thickness of less than 2 microns, a second layer of a support material which permits passage of low molecular weight substances but excludes high molecular weight substances, said support material having a thickness of between 1 and 20 microns, and an enzyme preparation positioned between and adhesively bonding said first and second layers.

6. A laminated membrane as set forth in claim 5 wherein the essentially homogeneous material is cellulose acetate having a thickness of 0.5 to 1.0 micron.

7. A laminated membrane as set forth in claim 6 wherein said second layer is a porous polycarbonate film having a thickness of approximately 5-7 microns, and the overall thickness of said membrane is less than 10 microns.

8. A laminated membrane as set forth in claim 7 further including an O-ring adhesively bonded to said second layer for purposes of attaching the membrane to a polarographic cell.

9. A laminated membrane a set forth in claim 7 wherein said enzyme is selected from the group consisting of uricase, glactose oxidase, and glucose oxidase.

* * * * *